United States Patent [19]

Shiba et al.

[11] 4,105,452
[45] Aug. 8, 1978

[54] MULTI-LAYERED COLOR PHOTOGRAPHIC LIGHT-SENSITIVE MATERIAL

[75] Inventors: Keisuke Shiba; Toshiaki Aono; Seiiti Kubodera; Takeshi Hirose; Reiichi Ohi; Tadao Shishido, all of Minami-ashigara, Japan

[73] Assignee: Fuji Photo Film Co., Ltd., Minami-ashigara, Japan

[21] Appl. No.: 672,922

[22] Filed: Apr. 2, 1976

Related U.S. Application Data

[63] Continuation of Ser. No. 494,955, Aug. 5, 1974, abandoned.

[30] Foreign Application Priority Data

Aug. 3, 1973 [JP] Japan .................................. 48-87723

[51] Int. Cl.² .......................... G03C 3/00; G03C 1/06; G03C 7/00
[52] U.S. Cl. .......................................... 96/74; 96/95; 96/55
[58] Field of Search ....................... 96/74, 95, 100, 22, 96/55, 107, 76

[56] References Cited

U.S. PATENT DOCUMENTS 3,582,333  6/1971  Yost .......................................... 96/74
3,620,746  11/1971  Barr .......................................... 96/74

OTHER PUBLICATIONS

Photographic Processing Chemistry, Mason, 1966, Focal Press, N.Y., pp. 210–211.

*Primary Examiner*—Edward C. Kimlin
*Attorney, Agent, or Firm*—Sughrue, Rothwell, Mion, Zinn and MacPeak

[57] ABSTRACT

A multi-layered color photographic light-sensitive material which comprises a support having thereon at least two light-sensitive silver halide emulsion layers which provide images having substantially different hues, with the light-sensitive material including 2-equivalent couplers and/or 4-equivalent anilinopyrazolone couplers and at least one of the light-sensitive silver halide emulsion layers or a colloidal layer of the light-sensitive material containing a hydroquinone derivative or a hydroquinone precursor substituted with a heterocyclic monothio group and an aliphatic monothio group, an aryl monothio group, an aliphatic oxy group, an aryloxy group or a heterocyclic oxy group and having a ballasting group containing 8 or more carbon atoms.

5 Claims, 13 Drawing Figures

LOG (THE AMOUNT OF EXPOSURE)

LOG (THE AMOUNT OF EXPOSURE)

LOG (THE AMOUNT OF EXPOSURE)

LOG (THE AMOUNT OF EXPOSURE)

LOG (THE AMOUNT OF EXPOSURE)

LOG (THE AMOUNT OF EXPOSURE)

FIG. 9
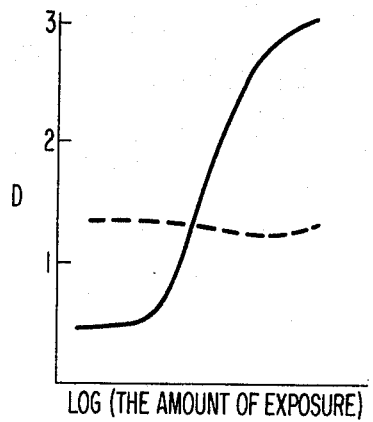
LOG (THE AMOUNT OF EXPOSURE)
FIG. 10
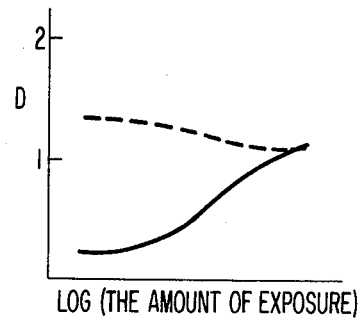
LOG (THE AMOUNT OF EXPOSURE)
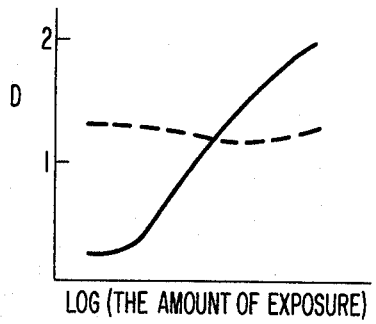
LOG (THE AMOUNT OF EXPOSURE)
FIG. 11
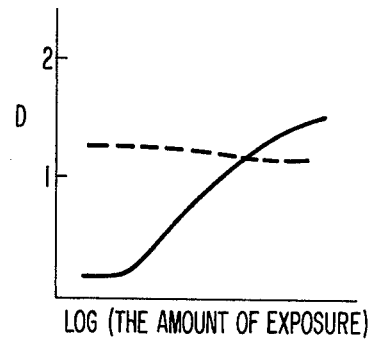
LOG (THE AMOUNT OF EXPOSURE)
FIG. 12
FIG. 13
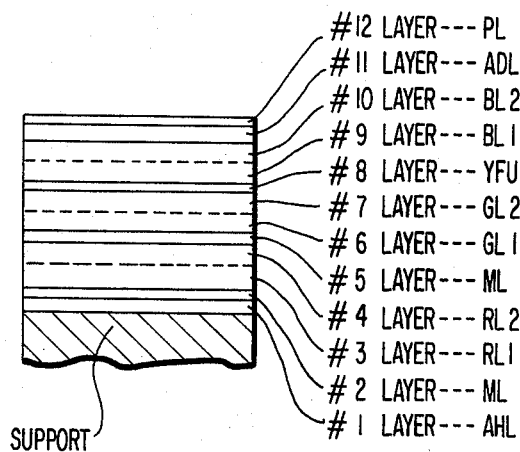
12 LAYER --- PL
11 LAYER --- ADL
10 LAYER --- BL 2
9 LAYER --- BL 1
8 LAYER --- YFU
7 LAYER --- GL 2
6 LAYER --- GL 1
5 LAYER --- ML
4 LAYER --- RL 2
3 LAYER --- RL 1
2 LAYER --- ML
1 LAYER --- AHL
SUPPORT

MULTI-LAYERED COLOR PHOTOGRAPHIC LIGHT-SENSITIVE MATERIAL

This is a continuation of application Ser. No. 494,955, filed Aug. 5, 1974 now abandoned.

BACKGROUND OF THE INVENTION

1. Field of the Invention

The present invention relates to a multi-layered color light-sensitive material and, more particularly, to a multi-layered color light-sensitive material whose color reproducibility, color image sharpness and graininess are improved by using a compound having specific chemical structure and characteristics capable of selectively providing an interlayer color-correcting effect.

2. Description of the Prior Art

Usually, a multi-layered color photographic light-sensitive material comprises two or more light-sensitive emulsion layer units, each of which light-sensitive emulsion layer unit performs an independent function. That is, conventional multi-layered color photographic light-sensitive materials comprise a support having provided thereon a cyan coupler-containing light-sensitive emulsion layer (RL) mainly sensitive to red light (visible light substantially longer than about 580 nm in wavelength), a magenta coupler-containing light-sensitive emulsion layer (GL) mainly sensitive to green light (visible light substantially about 500 to 600 nm in wavelength) and a yellow coupler-containing light-sensitive emulsion layer (BL) mainly sensitive to blue light (light substantially shorter than about 500 nm in wavelength). In addition, an interlayer (ML), a filter layer (FL) for filtering out light in the ultraviolet region or of a particular wavelength region, an antihalation layer (AHL), an interlayer performing a masking function (ML), a protective layer (PL) and the like are provided so that each of the above-described light-sensitive emulsion layer units can perform its own independent function.

It is known to use colored couplers, the so-called "DIR couplers, DIR-hydroquinone derivatives and DIR uncolored couplers" and the like, in order to improve color reproducibility. These couplers are described in, e.g., U.S. Pat. Nos. 2,449,966; 2,455,170; 2,600,788; 2,428,054; 3,148,062; 2,983,608; British Pat. No. 1,044,778 and related patents for improvements, C. R. Barr, J. R. Thirtle and P. W. Vittum, *Photographic Science and Eng.*, vol. 13, pp. 74 - 80 (1969), ibid, pp. 214 - 217 (1969), U.S. Pat. Nos. 3,277,554; 3,620,746; 3,379,529; 3,632,345 and; 3,622,328.

Colored couplers have the serious defect that the couplers themselves are colored. With DIR couplers, since they themselves form color dyes upon color development, they are severely restricted in chemical structure so that the characteristics of the color dyes themselves can satisfy various requirements for color image forming materials, and are restricted in usage (including the method for removing the color dyes from the light-sensitive material). In addition, DIR couplers heretofore obtained have the defect that they are chemically unstable. The so-called "DIR uncolored couplers" possess the defect that they are poor in coupling activity in color development.

The so-called "DIR hydroquinone derivatives" thus far known are too low in DIR activity (Development Inhibitor Releasing Activity) in a conventionally employed color developer, although they possess the advantage that they can be applied to any kind of light-sensitive emulsion layers and colloidal layers. Furthermore, they couple with an aromatic primary amine developing agent (e.g., the p-phenylenediamine series or p-aminophenol series) to form a cyan dye as a by-product (this being called "abnormal coloration"). Also, DIR hydroquinone derivatives must be immobilized in a given light-sensitive layer or colloidal layer and must be protected from light-sensitive silver halide grains, which is generally difficult. Otherwise, DIR hydroquinone couplers would function as a so-called "IRD (Inhibitor Releasing Developer)", and stable, strong interlayer interimage effect and the effect of improving color image sharpness could not be attained. It has been found that, where hydroquinone derivatives are used in a multi-layered light-sensitive material, immobilized in a specific colloidal layer only insufficiently and not protected from light-sensitive silver halide grains, the interlayer interimage effect which can essentially occur between the light-sensitive emulsion layers is seriously reduced in general.

SUMMARY OF THE INVENTION

An object of the present invention is to remove the above-described defects and, in particular, to provide a multi-layered color photographic light-sensitive material which contains a hydroquinone derivative for interlayer color correction (I.C.C.) having a high DIR activity and which possesses improved color reproducibility.

Another object of the present invention is to provide a novel hydroquinone derivative for interlayer color correction capable of removing "abnormal coloration".

A further object of the present invention is to provide a multi-layered color photographic light-sensitive material containing a novel hydroquinone derivative capable of being fixed or immobilized in a specific light-sensitive emulsion layer or a colloidal layer and capable of being protected from light-sensitive silver halide grains.

Still a further object of the present invention is to improve the method of using couplers so that the novel hydroquinone derivative for interlayer color correction can exhibit high "DIR activity".

Still a further object of the present invention is to improve a method for forming color images in a multi-layered color photographic light-sensitive material containing the novel interlayer color-correcting hydroquinone derivative.

These and other objects will become apparent from the description contained in this specification.

The above-described objects of the present invention have been attained by a multi-layered color photographic light-sensitive material which comprises a support having provided thereon at least two light-sensitive emulsion layers which provide images having sufficiently different hues and which light-sensitive material preferably contains in any of these light-sensitive emulsion layers a 2-equivalent coupler or a 4-equivalent anilino magenta coupler, at least one of the light-sensitive emulsion layers and colloidal layers containing a hydroquinone derivative or a hydroquinone precursor thereof substituted with a hetero ring monothio group and an aliphatic monothio group, an arylmonothio group, an aliphatic oxy group or an aryloxy group and containing a ballasting group having 8 or more carbon atoms.

BRIEF DESCRIPTION OF THE DRAWINGS

FIGS. 1, 7 and 13 show embodiments of the configuration of the multi-layered composition of the invention.

FIGS. 2 to 6 and 8 to 12 show the relationship between log (exposure amount) and density (D).

DETAILED DESCRIPTION OF THE INVENTION

Figure 1:
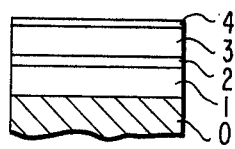

The interlayer color-correcting (I.C.C.) hydroquinone derivatives to be used in the present invention are compounds which release a diffusible development restrainer in color development in accordance with image development, selectively restrain color development of an adjacent light-sensitive emulsion layer and, as a result, perform an interlayer color-correcting effect. Preferably, they are hydroquinone derivatives or precursors thereof which bear a hetero ring monothio group capable of becoming a development restrainer and are substituted with an aliphatic thio group or an aliphatic oxy group having 8 or more carbon atoms which functions at the same time as a ballasting group. Preferably, they are the compounds represented by the following general formula (I);

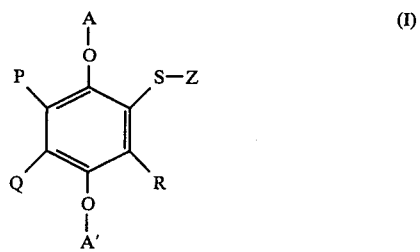

(I)

wherein A and A' each represents a hydrogen atom or a group capable of being eliminated by an alkali (e.g., an alkoxycarbonyl group, an acyl group or an alkoxalyl group), and A' may combine with R or Q to form a ring (e.g., an oxathiole ring); P, Q or R each represents a hydrogen atom, an alkyl group (e.g., having 1 to 32 carbon atoms, such as a methyl group, an ethyl group, a 1,1,3,3-tetramethylbutyl group or an n-pentadecyl group), an aryl group (e.g., a phenyl group or a p-tolyl group), an —S—Y residue [with Y being an alkyl group (e.g., having 1 to 8 carbon atoms, such as a 2-ethylhexyl group, an n-dodecyl group, a hexadecyl group, an n-octadecyl group, a hydroxycarbonylmethyl group, an ethoxycarbonylmethyl group or a 2-hydroxyethyl group), or an aryl group (e.g., a phenyl group)], a hydroxy group, a halogen atom, an —S—Z residue, an alkoxy group or an aryloxy group (e.g., an —O—Y group with Y having the same meaning as above defined), or a heterocyclic ring; Z represents a heterocyclic ring residue photographically substantially inert in a bonded state and, particularly, it represents a tetrazolyl group (e.g., a 1-phenyltetrazolyl group), a triazolyl group (e.g., a 4-phenyl-1,2,4-triazol-5-yl group or a 3-n-pentyl-4-phenyl-1,2,4-triazol-5-yl group), a thiadiazolyl group (e.g., a 2-methylthio-1,3,4-thiadiazol-5-yl group or a 2-amino-1,3,4-thiadiazol-5-yl group), an oxadiazolyl group (e.g., a 2-phenyl-1,3,4-oxadiazol-5-yl group), a tetrazaindenyl group (e.g., a 6-methyl-1,3,3a,7-tetrazainden-4-yl group or a 6-n-nonyl-1,3,3a,7-tetrazainden-4-yl group), an oxazolyl group (e.g., a benzoxazol-2-yl group), a thiazolyl group (e.g., a benzothiazol-2-yl group), or the like. In particular, among P, Q and R, R can be an —S—Z residue. A ballasting group is contained in the chemical structure of the molecule, preferably in the chemical structure of P, Q or R, and at least one of P, Q and R is a Y—S— residue.

The ballasting group in the I.C.C. hydroquinone derivative to be used in the present invention means an aliphatic residue having about 8 to about 32 carbon atoms for ballasting.

A first feature of the hydroquinone derivative of the present invention, and, in particular, of the compound represented by the general formula (I) lies in the Y—S— residue. In general, the reducing property or the DIR activity of the hydroquinone derivatives tend to be reduced by the introduction of a Z—S— residue. On the other hand, the introduction of a Y—S— residue (preferably, Y being an aliphatic residue) tends to increase the reducing property or the DIR activity of the hydroquinone derivatives.

A second feature of the invention is that when the ballasting group, preferably the Y— residue, is an aliphatic group having about 8 or more carbon atoms, the so-called "abnormal coloration" can be prevented and ballasting properties can be provided. On the other hand, "abnormal coloration" due to the hydroquinone derivative can be prevented by providing a substituent in the 3- or 4-position.

A third feature is that the affinity of the hydroquinone derivative for an organic solvent, couplers, hydroquinone derivatives, an ultraviolet absorbent and the like to be used at the same time can be increased by the introduction of a Y—S— residue.

A fourth feature is that the hydroquinone derivatives by the present invention can be synthesized and produced comparatively easily.

Other features of the invention will be understood from the additional descriptions of the invention given hereinafter.

Several examples of the compounds of the invention are illustrated below.

| Compound-1 | |
|---|---|
| 2-n-Dodecylthio-5-(1'-phenyltetrazol-5'-ylthio)hydroquinone | m.p. 131 – 2° C |
| Compound-2 | |
| 2-n-Octadecylthio-5-(1'-phenyltetrazol-5-ylthio)hydroquinone | m.p. 132 – 3° C |
| Compound-3 | |
| 2-n-Hexadecylthio-5-(1'-phenyltetrazol-5-ylthio)hydroquinone | m.p. 129 – 131° C |
| Compound-4 | |
| 2-[2',5'-Dihydroxy-6'-(1''-phenyltetrazol-5''-ylthio)-4'-(1''',1''',3''',3'''-tetramethylbutyl)]phenylthiobenzoic acid | d.p. 196° C |
| Compound-5 | |
| 2-[2',5'-Dihydroxy-6'-(1''-phenyltetrazol-5''-ylthio)-3'-(1''',1''',3''',3'''-tetramethylbutyl)]phenylthiobenzoic acid | d.p. 182 – 3° C |
| Compound-6 | |
| 2-(1'-Phenyltetrazol-5'-ylthio)-3-phenylthio-6-(1'',1'',3'',3''-tetramethylbutyl)hydroquinone | m.p. 147° C |
| Compound-7 | |
| 2-(1'-Phenyltetrazol-5'-ylthio)-3-phenylthio-5-(1'',1'',3'',3''-tetramethylbutyl)hydroquinone | m.p. 148 – 9° C |
| Compound-8 | |
| 2,5-Dihydroxy-5-(1'-phenyltetrazol-5'-ylthio)-4-(1'',1'',3'',3''-tetramethylbutyl)phenylthioacetic acid | m.p. 133° C |
| Compound-9 | |
| 2-[2',5'-Dihydroxy-3'-n-hexadecylthio-6'-(1''-phenyltetrazol-5''-ylthio)]phenylthiobenzoic acid | d.p. 143 – 5° C |
| Compound-10 | |
| 2-n-Hexadecylthio-5-(1'-phenyltetrazol-5'-ylthio)-6-phenylthiohydroquinone | |

Compound-11
4-(1'-Phenyltetrazol-5'-ylthio)-5-hydroxy-7-(1'',1'',3'',3''-tetramethylbutyl)benzoxathiol-2-one m.p. 94 – 6° C

Compound-12
2-[2',5'-Dihydroxy-6'-(1''-phenyltetrazol-5''-ylthio)-3'-(1''',1''',3''',3'''-tetramethylbutyl)]phenylthiobenzoic acid methyl ester m.p. 176° C

Compound-13
2-[2',5'-Dihydroxy-6'-(1''-phenyltetrazol-5''-ylthio)-4'-(1''',1''',3''',3'''-tetramethylbutyl)]phenylthiobenzoic acid methyl ester m.p. 106 – 7° C

Compound-14
2-[2',5'-Dihydroxy-3'-n-pentadecylthio-6'-(1''-phenyltetrazol-5''-ylthio)]phenylthiobenzoic acid methyl ester d.p. 197° C

Compound-15
2-n-Octyloxycarbonylmethylthio-6-phenyl-3-(1'-phenyltetrazol-5'-ylthio)hydroquinone d.p. 93 – 5° C

Compound-16
2-p-Nitrophenylthio-3-(1'-phenyltetrazol-5'-ylthio)-6-(1'',1'',3'',3''-tetramethylbutyl)hydroquinone d.p. 113 – 5° C

Compound-17
2-(2'-Methylthio-1',3',4'-thiadiazol-5'-ylthio)-6-(1'',1'',3'',3''-tetramethylbutyl)hydroquinone m.p. 173 – 4° C

Compound-18
3-(2'-Methylthio-1',3',4'-thiadiazol-5'-ylthio)-6-(1'',1'',3'',3''-tetramethylbutyl)hydroquinone m.p. 163° C

Compound-19
2,3-bis(2'-Methylthio-1',3',4'-thiadiazol-5-ylthio)-6-(1'',1'',3'',3''-tetramethylbutyl)hydroquinone m.p. 220° C

Compound-20
2-(3'-n-Pentyl-4'-phenyl-1',2',4'-triazol-5'-ylthio)-5-(1'',1'',3'',3''-tetramethylbutyl)hydroquinone m.p. 202° C

Compound-21
2-(6'-Methyl-1',3',3a',7'-tetrazainden-4'-ylthio)-6-(1'',1'',3'',3''-tetramethylbutyl)hydroquinone m.p. 198° C

Compound-22
2,3-bis(6'-Methyl-1',3',3a',7'-tetrazainden-4'-ylthio)-6-(1'',1'',3'',3''-tetramethylbutyl)hydroquinone m.p. 228° C

Compound-23
2-n-Hexadecylthio-5-(2'-methylthio-1',3',4'-thiadiazol-5'-ylthio)hydroquinone m.p. 215° C

Compound-24
2-[2',5'-Dihydroxy-6'-(2''-methylthio-1''',4''-thiadiazol-5''-ylthio)-3'-(1''',1''',3''',3'''-tetramethylbutyl)]-phenylthiobenzoic acid m.p. 120° C

Compound-25
2-(2'-Amino-1',3',4'-thiadiazol-5'-ylthio)-5-(1'',1'',3'',3''-tetramethylbutyl)hydroquinone m.p. 193 – 4° C

Compound-26
2-[2',5'-Dihydroxy-6'-(2''-amino-1''',4''-thiadiazol-5''-ylthio)-5-(1''',1''',3''',3'''-tetramethylbutyl)]-phenylthiobenzoic acid m.p. 243° C

Compound-27
2-(2'-Amino-1',3',4'-thiadiazol-5'-ylthio)-3-n-dodecylthio-6-(1'',1'',3'',3''-tetramethylbutyl)hydroquinone m.p. 203° C

Compound-28
2-(6'-t-Butyl-1,3,3a,7-tetrazainden-4-ylthio)-6-(1'',1'',3'',3''-tetramethylbutyl)hydroquinone m.p. 127° C

Compound-29
2-(6'-n-Nonyl-1',3',3a',7'-tetrazainden-4'-ylthio)-6-(1'',1'',3'',3''-tetramethylbutyl)hydroquinone m.p. 144° C

Compound-30
2-(4'-Phenyl-1',2',4'-triazol-5'-ylthio)-2-(1'',1'',3'',3''-tetramethylbutyl)hydroquinone m.p. 162 – 3° C

Compound-31
2-(2'-Phenyl-1',3',4'-oxadiazol-5-ylthio)-5-(1'',1'',3'',3'',3''-tetramethylbutyl)hydroquinone m.p. 230° C 3''-tetramethylbutyl)hydroquinone m.p. 190° C

Compound-32
2-(1'-Phenyltetrazol-5'-ylthio)-5-n-octyloxycarbonylmethylthiohydroquinone

Compound-33
2-t-Dodecylthio-5-(1'-phenyltetrazol-5'-ylthio)hydroquinone

Compound-34
2-(Benzoxazol-2'-ylthio)-5-n-octadecylhydroquinone

Compound-35
2-(2'Methylphenylthio)-6-n-octadecylthio-3-(1'-phenyltetrazol-5''-ylthio)hydroquinone

Compound-36
2-n-Octyloxycarbonylmethylthio-3-(1'-phenyltetrazol-5'-ylthio)-6-p-tolylhydroquinone

Compound-37
2-Ethoxycarbonylmethylthio-6-n-hexadecylthio-3-(1'-phenyltetrazol-5'-ylthio)hydroquinone

Compound-38
2-Phenylthio-3-(1'-phenyltetrazol-5'-ylthio)-5-n-dodecylthiohydroquinone The compounds represented by the general formula (I) can be synthesized according to the process described in U.S. Pat. No. 3,379,529, i.e., by the addition reaction of a mercapto compound to a benzoquinone.

The general synthetic process will be described by the following specific examples. Unless otherwise indicated herein, all parts, percents, ratios and the like are by weight.

SYNTHESIS EXAMPLE 1

316 g of 2-n-hexadecylthio-p-benzoquinone was dissolved in 1 liter of methanol and stirred under cooling with ice. To this mixture was gradually added dropwise a solution prepared by dissolving 155 g of 1-phenyl-5-mercaptotetrazole in 800 ml of methanol. After the completion of the dropwise addition, the mixture was stirred for 3 hours under cooling with ice. Then, upon continuing the stirring for 8 hours at room temperature, there were precipitated crystals.

The thus formed crystals were collected by filtration and recrystallized from benzene. Thus, 350 g of 2n-hexadecylthio-5-(1'-phenyltetrazol-5-ylthio)hydroquinone was obtained. Yield: 350 g; m.p. 129° – 131° C.

SYNTHESIS EXAMPLE 2 (Compound 6)

15 g of 2-(1'-phenyltetrazol-5-ylthio)-6-(1'',1'',3'',3''-tetramethylbutyl)-p-benzoquinone was added to 150 ml of methanol and stirred under cooling with ice. To this was added dropwise a solution prepared by dissolving 4.5 g of thiophenol in 25 ml of methanol. After the dropwise addition, the mixture was stirred for 3 hours under cooling with ice. The thus formed crystals were collected by filtration and recrystallized from a mixed solvent of hexane and ethyl acetate. Thus, 7.5 g of 2-(1'-phenyltetrazol-5'-ylthio)-3-phenylthio-6-(1'',1'',3'',3''-tetramethylbutyl)hydroquinone having a melting point of 147° C was obtained. Yield: 7.5 g; m.p. 147° C.

SYNTHESIS EXAMPLE 3 (Compound 20)

13 g of 3-mercapto-5-n-pentyl-4-phenyl-1,2,4-triazole was dissolved in 200 ml of methanol and stirred under cooling with ice. To this was added portionwise 12 g of 2-(1',1',3',3'-tetramethylbutyl)-p-benzoquinone. After the addition, the mixture was stirred for 2 hours under cooling with ice, then left overnight at room temperature (about 20° – 30° C). Methanol was removed under reduced pressure, and diethyl ether was added to the resulting residue. The thus precipitated crystals were collected by filtration and recrystallized from ethyl acetate.

Thus, 5 g of 2-(3'-n-pentyl-4'-phenyl-1,2,4-triazol-5'-ylthio)-5-(1",1",3",3"-tetramethylbutyl)hydroquinone having a melting point of 198° C was obtained. Yield: 5 g; m.p. 198° C.

The couplers usable in the present invention are 4- or 2-equivalent couplers, particularly ballasted couplers which are used as a photographic element. It has been discovered that the combined use of the I.C.C. hydroquinone derivative of the present invention and a coupler having specific chemical structure gives rise to a specifically strong "DIR Effect". The present invention is based on this discovery.

Couplers particularly useful for the present invention are represented by the following general formulae (II), (III), (IV), (V) and (VI);

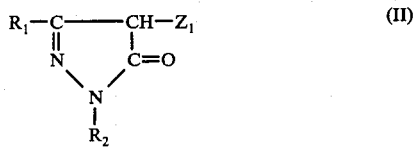
(II)

wherein $R_1$ represents an alkyl group selected from primary, secondary and tertiary alkyl groups (e.g., a methyl group, a propyl group, a n-butyl group, a t-butyl group, a hexyl group, a 2-hydroxyethyl group or a 2-phenylethyl group), an alkoxy group (e.g., a methoxy group, an ethoxy group or a benzyloxy group), an aryloxy group (e.g., a phenoxy group), an aryl group, a heterocyclic ring (e.g., a quinolinyl group, a pyridyl group, a benzofuranyl group or an oxazolyl group), an amino group (e.g., a methylamino group, a diethylamino group, a dibutylamino group, a phenylamino group, a tolylamino group, a 4-(3-sulfobenzamino)anilino group, a 2-chloro-4-acylaminoanilino group, a 2-chloro-5-alkoxycarbonylanilino group, a 2-trifluoromethylphenylamino group or a cycloalkylamino group), a carbonamido group (e.g., an alkylcarbonamido group such as an ethylcarbonamido group, an arylcarbonamido group, a heterocyclic carbonamido group such as a benzothiazolylcarbonamido group, a sulfonamido group or a heterocyclic sulfonamido group), an ureido group (e.g., an alkylureido group, an arylureido group or a heterocyclic ureido group); $R_2$ represents an aryl group (e.g., a naphthyl group, a phenyl group, a 2,4,6-trichlorophenyl group, a 2-chloro-4,6-dimethylphenyl group, a 2,6-dichloro-4-methoxyphenyl group, a 4-methylphenyl group, a 4-acylaminophenyl group, a 4-alkylaminophenyl group, a 4-trichloromethylphenyl group or a 3,5-dibromophenyl group), a heterocyclic group (e.g., a benzofuranyl group, a naphthoxazolyl group or a quinolinyl group), an alkyl group selected from primary, secondary and tertiary alkyl groups (e.g., a methyl group, an ethyl group, a t-butyl group or a benzyl group), or the like; $Z_1$ represents a group capable of being eliminated upon color development, such as an acyloxy group, an aryloxy group, a halogen atom, a thiocyano group, a di-substituted amino group, an amido group (e.g., an alkylsulfonamido group, an arylsulfonamido group, a heterocyclic sulfonamido group, an alkylcarbonamido group or an arylcarbonamido group, an aryloxycarbonyloxy group, an alkoxycarbonyloxy group, a benzotriazolyl group, an indazolyl group, an arylazo group or a hetero ring azo group (examples of these being described in U.S. Pat. Nos. 3,227,550; 3,252,924; 3,311,476; 3,419,391; German Patent OLS 2,015,867; and U.S. Patent Application Ser. No. 471,639, filed May 20, 1974), or else, $Z_1$ represents a residue capable of releasing a development restrainer upon development, such as an arylmonothio group (e.g., a 2-aminophenylthio group or a 2-hydroxycarbonylphenylthio group), a heterocyclic ring monothio group (e.g., a tetrazolyl group, a triazinyl group, a triazolyl group, an oxazolyl group, an oxadiazolyl group, a diazolyl group, a thiazyl group or a thiadiazolyl group), a heterocyclic imido group (e.g., a 1-benzotriazolyl group, a 1-indazolyl group or a 2-benzotriazolyl group) (for example, those groups which are described in U.S. Pat. Nos. 3,148,062; 3,227,554; 3,615,506; and 3,701,783 being suitably employed).

Where $Z_1$ in the above formula is a hydrogen atom, $R_1$ represents an amino group. Such compounds are the so-called 4-equivalent couplers and show specifically strong "DIR Effect". This is an effect which has so far been absolutely unknown. Of these compounds, preferred examples are those compounds represented by the following general formula (III);

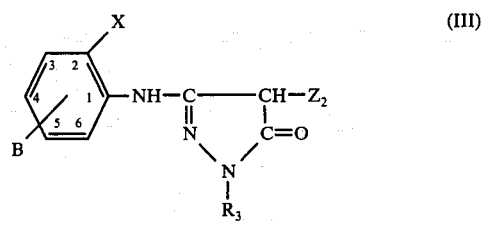
(III)

wherein $R_3$ represents an aryl group (e.g., a phenyl group, a 2-chlorophenyl group, a 4-chlorophenyl group, a 2,5-dichlorophenyl group, a 2,6-dichlorophenyl group, a 2,4,6-trichlorophenyl group, a 2-bromophenyl group, a 2-cyanophenyl group, a 4-cyanophenyl group, a 3-nitrophenyl group, a 4-nitrophenyl group, a 4-methylphenyl group, a 2,6-dimethylphenyl group, a 4-butylphenyl group, a 2-trifluoromethylphenyl group, a 2-ethoxyphenyl group, a 4-phenylphenyl group, a 4-phenoxyphenyl group, an N-methylbenzamidophenyl group, an N,N-diphenylcarbamylphenyl group, an N,N-diphenylsulfamylphenyl group, an N,N-dibutylsulfamylphenyl group, a phenyl-N-methylsulfonamidophenyl group, a 2-methyl-5-nitrophenyl group, a 2-chloro-5-cyanophenyl group, a 5-chloro-2-methylphenyl group, a 2,6-dichloro-4-methylphenyl group, a 2,4-dichloro-6-methylphenyl group, a 2-chloro-4,6-dimethylphenyl group, a 2,6-dichloro-4-methoxyphenyl group, a 2,6-dichloro-4-nitrophenyl group, a 2,4,6-trimethyl-3-nitrophenyl group or a 2,4,6-trimethyl-3-substituted aminophenyl group) or a heterocyclic ring (e.g., a 2-thiazolyl group, a 2-benzothiazolyl group, a 2-benzoxazolyl group, a 2-oxazolyl group, a 2-imidazolyl group, a 2-benzimidazolyl group or a like 5- or 6-membered heterocyclic group), or the like; $Z_2$ represents a hydrogen atom or the same eliminatable group as defined with respect to $Z_1$; B represents a ballasting group (a residue having about 8 to about 32 carbon atoms so as to ballast the coupler, specific examples thereof being described hereinafter); and X represents an alkoxy group having 1 to 18 carbon atoms or a halogen atom (e.g., a fluorine atom, a chlorine atom or a bromine atom).

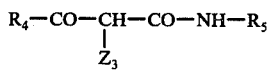  (IV)

In the above general formula (IV), $R_4$ represents an alkyl group selected from primary, secondary and tertiary alkyl groups (e.g., a t-butyl group, a 1,1-dimethylpropyl group or a 1,1-dimethyl-1-methoxyphenoxymethyl group), an aryl group (e.g., a phenyl group, an alkylphenyl group such as a 3-methylphenyl group or a 3-octadecylphenyl group, an alkoxyphenyl group such as a 2-methoxyphenyl group or a 4-methoxyphenyl group, a halophenyl group, a 2-halo-5-alkamidophenyl group, a 2-chloro-5-[α-(2,4-di-t-amylphenoxy)butyramido]phenyl group, a 2-methoxy-5-alkamidophenyl group or a 2-chloro-5-sulfonamidophenyl group); $R_5$ represents an aryl group (e.g., a 2-chlorophenyl group, a 2-halo-5-alkamidophenyl group, a 2-chloro-5-[α-(2,4-di-t-amylphenoxy)acetamido]phenyl group, a 2-chloro-5-(4-methylphenylsulfonamido)phenyl group or a 2-methoxy-5-(2,4-di-t-amylphenoxy)acetamidophenyl group); $Z_3$ represents a group capable of being eliminated upon color development, such as a halogen atom (particularly a fluorine atom), an acyloxy group, an aryloxy group, a heteroaromatic carbonyl group, a hydroxy group, a sulfimido group, an alkylsulfoxy group, an arylsulfoxy group, a phthalimido group, a dioxoimidazolidinyl group, a dioxoxazolidinyl group, an indazolyl group or a dioxothiazolidinyl group, etc. These are described in, e.g., U.S. Pat. Nos. 3,227,550; 3,253,924; 3,277,155; 3,265,506; 3,408,194; 3,415,652; French Pat. No. 1,411,384; British Pat. Nos. 944,490; 1,040,710; 1,118,028; German Pat. Nos. OLS 2,057,941; 2,163,812; 2,213,461; and 2,219,971. Also, $Z_3$ represents a residue capable of releasing a development restrainer, such as an arylmonothio group (e.g., a phenylthio group or a 2-carboxylphenylthio group), a heterocyclic ring thio group, a 1-benzotriazole group or a 1-benzodiazole group and, in particular, the groups described in U.S. Pat. No. 3,933,500.

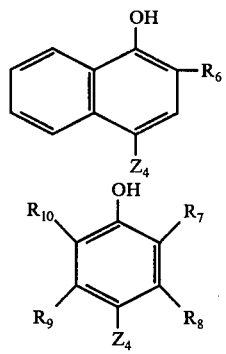

In the above formulae (V) and (VI), $R_6$ represents a substituent usually used for cyan couplers, such as a carbamyl group (e.g., an alkylcarbamyl group, an arylcarbamyl group such as a phenylcarbamyl group, a heterocyclic carbamyl group such as a benzothiazolylcarbamyl group), a sulfamyl group (e.g., an alkylsulfamyl group, an arylsulfamyl group such as a phenylsulfamyl group or a heterocyclic sulfamyl group), an alkoxycarbonyl group, an aryloxycarbonyl group or the like; $R_7$ represents an alkyl group, an aryl group, a heterocyclic group, an amino group (e.g., an amino group, an alkylamino group or an arylamino group), a carbonamido group (e.g., an alkylcarbonamido group or an arylcarbonamido group), a sulfonamido group, a sulfamyl group (e.g., an alkylsulfamyl group or an arylsulfamyl group), a carbamyl group or the like; $R_8$, $R_9$ and $R_{10}$ each represents a group defined with respect to $R_7$, a halogen atom, an alkoxy group or the like; $Z_4$ represents a group capable of being eliminated upon color development, i.e., a group defined with respect to $Z_1$, a halogen atom (e.g., a chlorine atom, a bromine atom or an iodine), an indazolyl group, a cyclic imido group, an acyloxy group, an aryloxy group, an alkoxy group, a sulfo group, an arylazo group, a heterocyclic azo group, or the like (examples of these groups being described in U.S. Pat. Nos. 2,423,730; 3,227,550; 3,311,476; British Pat. No. 1,084,480; and 1,165,563).

Also, the couplers of the present invention can be colored couplers. Such colored couplers are described in, e.g., U.S. Pat. Nos. 2,983,608; 3,005,712; 3,034,892; British Pat. Nos. 936,621; 1,269,073; 586,211; 627,814; French Pat. Nos. 980,372; 1,091;903; 1,257,887; 1,398,308; and 2,015,649.

The couplers to be used in the present invention are advantageously ballasted. In order to ballast the couplers, a group containing a hydrophobic residue having about 8 to 32 carbon atom is introduced into the coupler molecule. Such a residue is called a ballasting group. The ballasting group can be connected to the skeletal structure of the coupler directly or through a linkage such as an imino linkage, an ether linkage, a carbonamido linkage, a sulfonamido linkage, an ureido linkage, an ester linkage, an imido linkage, a carbamoyl linkage, a sulfamoyl linkage, or the like.

Several specific examples of the ballasting group are described in the specific examples of the couplers of the present invention.

Specific examples of ballasting groups which are suitable are as follows.

(I) Alkyl groups and alkenyl groups, such as;
—$CH_2$—$CH(C_2H_5)_2$, —$C_{12}H_{25}$, —$C_{16}H_{33}$, —$C_{17}H_{33}$ (II) Alkoxyalkyl groups such as;

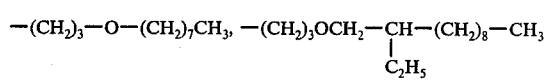

as described in Japanese Patent Publication No. 27536/64

(III) Alkylaryl groups such as;

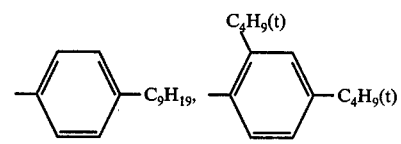

(IV) Alkylaryloxyalkyl groups such as;

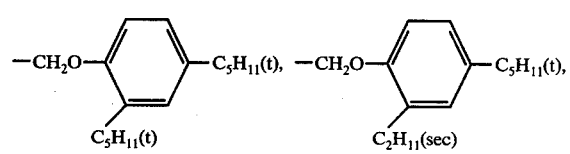

-continued

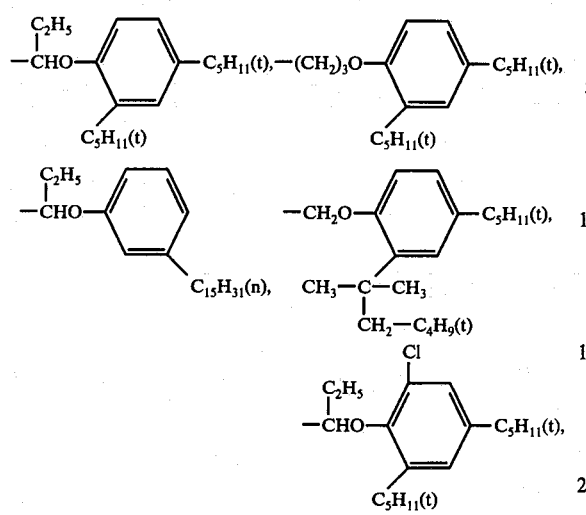

(V) Acylamidoalkyl groups such as;

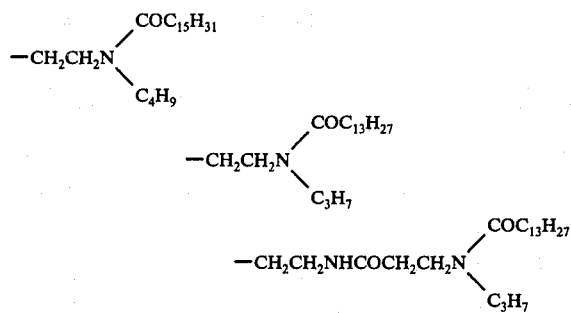

as described in U.S. Pat. Nos. 3,333,344 and 3,418,129

(VI) Alkoxyaryl groups and aryloxyaryl groups such as;

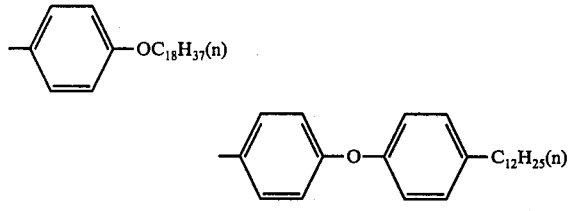

(VII) Residues having a long-chain aliphatic, alkyl or alkenyl group and a water-solubilizing carboxy or sulfo group, such as;

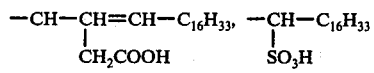

(VIII) Ester-substituted alkyl groups such as;

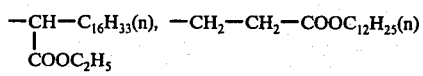

(IX) Aryl- or heterocyclic ring-substituted alkyl groups such as;

—CH$_2$—CH$_2$—◯—NHCOCH$_2$CH—C$_{18}$H$_{37}$(n),
                                    |
                                    COOCH$_3$

—CH$_2$CH$_2$—◯—N(pyrrolidine-2,5-dione with C$_{18}$H$_{37}$(n)), (X) Aryloxyalkoxycarbonyl-substituted aryl groups such as;

—◯—COOCH$_2$CO—◯(C$_5$H$_{11}$(t), C$_5$H$_{11}$(t))
         |
        CH$_3$
        |
        CH$_3$

In particular, when used in combination with the I.C.C. hydroquinone derivative represented by the general formula (I), couplers selected from those couplers represented by the general formulae (II), (IV), (V) and (VI) show a specifically strong, "DIR Effect" as compared with 4-equivalent couplers having corresponding chemical structures. However, this mechanism has not heretofore been clearly understood. While not desiring to be bound, it is believed that since oxidized color-developing agent does not require oxidation of a reducing color dye of a leuco form in the coupling between the 2-equivalent coupler and an aromatic primary amine derivative to form a color dye, it accelerates the exchange oxidation with the I.C.C. hydroquinone derivatives. Also, the mechanism how the coupler represented by the general formula (III) shows a particularly remarkable "DIR Effect" is not at present known.

Specific examples of couplers which can be used in the invention are given below. However, the present invention is not to be construed to be limited in any way to these couplers.

Yellow Couplers

[Y-2] α-(2,4-Dioxo-5,5-dimethyloxazolidinyl)-α-pivaloyl-2-chloro-5-[α-(2,4-di-tert-amylphenoxy)-butyramido]-acetanilide

[Y-2] α-(4-Carboxyphenoxy)-α-pivaloyl-2-chloro-5-[α-(2,4-di-tert-amylphenoxy)butyramido]acetanilide

[Y-3] α-[3-(1-Benzyl-2,4-dioxo)hydantoin]-α-pivaloyl-2-methoxy-5-[α-(2,4-di-tert-amylphenoxy)-butyramido]acetanilide

[Y-4] α-Benzoyl-α-(2-benzothiazolylthio)-4-[N-(γ-phenylpropyl)-N-(4-tolyl)sulfamyl]acetanilide

[Y-5] α-[3-(1-Benzyl-2,4-dioxo)hydantoin]-α-pivaloyl-2-chloro-5-[α-(2,4-di-tert-amylphenoxy)-butyramido]acetanilide

[Y-6] α-Benzoyl-α-(5- or 6-bromo-1-benzotriazolyl)-5-[α-(2,4-di-tert-amylphenoxy)propionamido]-2-chloro-acetanilide

[Y-7] α-(4-Methoxybenzoyl)-α-[3-(2,4-dioxohydantoin]-2-chloro-5-[α-(2,4-di-tert-amylphenoxy)-butyramido]acetanilide

[Y-8] α-Octadecanoyl-α-(5- or 6-bromo-1-benzotriazolyl)-2,5-dimethoxyacetanilide

[Y-9] α-(4-Methoxybenzoyl)-α-(3,5-dioxomorpholino)-5-[γ-(2,4-di-tert-amylphenoxy)butyramido[-2-chloroacetanilide

Magenta Couplers

[M-1] 1-(2,4,6-Trichlorophenyl)-3-[3-{α-(2,4-di-tert-amylphenoxy)acetamido}benzamido]-4-acetoxy-5-pyrazolone

[M-2] 1-(2,4,6-Trichlorophenyl)-3-hexadecaneamido-4-(4-hydroxyphenyl)azo-5-pyrazolone

[M-3] 1-(2,4,6-Trichlorophenyl)-3-(2-chloro-5-tridecanoylamino)anilino-5-pyrazolone

[M-4] 1-(2,4,6-Trichlorophenyl)-3-(2-chloro-5-tetradecyloxycarbonyl)anilino-4-(1-naphthylazo)-5-pyrazolone

[M-5] 1-(2,4-Dichloro-6-methoxyphenyl)-3-[(2-chloro-5-tridecanoylamino)anilino]-4-benzyloxycarbonyloxy-5-pyrazolone

[M-6] 1-[4-{α-(2,4-Di-tert-amylphenoxy)acetamido}phenyl]-3-(4-methoxyanilino)-4-(5- or 6-bromo-1-benzotriazolyl)-5-pyrazolone

[M-7] 1-(2,4,6-Trichlorophenyl)-3-[3-{(2,4-di-tert-amylphenoxy)acetamido}benzamido]-4-piperidino-5-pyrazolone

[M-8] 1-(2,4,6-Trichlorophenyl)-3-[3-(2,4-di-tert-amylphenoxyacetamido)benzamido]-4-ethoxycarbonyloxy-5-pyrazolone

[M-] 1-Benzyl-3-[2-chloro-5-(tetradecanamido)anilino]-4-(5-or 6-methyl-1-benzotriazolyl)-5-pyrazolone

[M-10] 1-[4-{α-(2,4-Di-t-amylphenoxy)acetamido}phenyl]-3-ethoxy-4-(5- or 6-bromo-1-benzotriazolyl)-5-pyrazolone

[M-11] 1-(2,4,6-Trichlorophenyl)-3-[3-{α-(2,4-di-tert-amylphenoxy)acetamido}benzamido]-4-phenylsulfonamido-5-pyrazolone

Cyan Couplers

[C-1] 1-Hydroxy-4-chloro-N-[α-(2,4-di-tert-amylphenoxy)butyl]-2-naphthamide

[C-2] 5-Methyl-4,6-dichloro-2-[α-(3-n-pentadecylphenoxy)butyramido]phenol

[C-3] 1-Hydroxy-4-iodo-N-dodecyl-2-naphthamide

[C-4] 5-Methoxy-2-[α-(3-n-pentadecylphenoxy)butyramido]-4-(1-phenyl-5-tetrazolylthio)phenol

[C-5] 1-Hydroxy-4-[2-(2-hexyldecyloxycarbonyl)phenylazo]-2-[N-(1-naphthyl]naphthamide

[C-6] 5-Methoxy-2-[α-(3-n-pentadecylphenoxy)butyramido]-4-(1-phenyl-5-tetrazolylthio)phenol The couplers of the present invention are roughly classified into two groups: one being Fischer type couplers having a water-solubilizing group such as a carboxyl group, a hydroxy group or a sulfo group; and the other being hydrophobic couplers.

As a method for the addition or dispersion of couplers into an emulsion or a method for the addition thereof to a gelatino-silver halide emulsion or hydrophilic colloid, those conventionally known in the art can be employed. For example, a method of mixing the coupler with a high boiling organic solvent (e.g., boiling above 170° C) such as dibutyl phthalate, tricresyl phosphate, a wax, a higher fatty acid or an ester thereof (particularly, a glycerol lower fatty acid ester, a citric acid aliphatic ester) for dispersion (as described in, e.g., U.S. Pat. Nos. 2,304,939; 2,322,027; and U.S. Pat. No. 3,936,303 filed on July 3, 1974 a method of mixing the coupler with a low-boiling organic solvent (e.g., boiling below 170° C) or a water-soluble organic solvent for dispersion, a method of dispersing the coupler using a high-boiling solvent in combination with them (as described in, e.g., U.S. Pat. Nos. 2,801,170; 2,801,171; and 2,949,360), and, when the coupler itself has a sufficiently low melting point (for example, less than 75° C), a method of dispersing the coupler alone (as described in, e.g., German Pat. No. 1,143,707) or in combination with other couplers to be used together, such as a colored coupler and an uncolored coupler can be employed.

The I.C.C. hydroquinone derivatives of the present invention can be dispersed for use in the same manner as the hydrophobic couplers. Preferably, they can be mixed with the hydrophobic coupler or with conventionally used hydroquinone derivatives and dispersed for use. The proportion of the I.C.C. hydroquinone derivative is preferably not more than 20% by weight based on the total amount of couplers used.

As the dispersing aid, conventionally used anionic surface active agents (e.g., sodium alkylbenzenesulfonates, sodium dioctylsulfosuccinate, sodium dodecylsulfate, sodium alkylnaphthalenesulfonate or Fischer type couplers), amphoteric surface active agents (e.g., N-tetradecyl-N,N-dipolyethylene-α-betaine), and nonionic surface active agents (e.g., sorbitan monolaurate) can be used.

The emulsion to be used in the present invention is a gelatino-silver halide photographic emulsion containing grains of silver chloride, silver bromide, silver iodide or a mixture thereof. Silver halide grains can possess the crystal habit of the (1 0 0) face, the (1 1 1) face or a mixture thereof, and can be regular grains or grains having a twin plane. The grain size can be about 0.04 μ to 2 μ.

The emulsion to be used in the present invention can be obtained using any of a single jet method, a double jet method, a triple jet method, a back mixing method and a conversion method. The hydrophilic colloid which can be used for the emulsion of the invention includes gelatin, cellulose derivatives, alginates, hydrophilic synthetic polymers (e.g., polyvinyl alcohol, polyvinyl pyrrolidone, polystyrene sulfonic acid, polyhydroxyethyl acrylate or polydiethylaminoethyl acrylate) and the like. Further, a plasticizer for improving the dimensional stability of films and a polymer latex such as polymethyl methacrylate, polyethyl acrylate, polybutyl acrylate, etc., can be used.

To the silver halide emulsion used in the present invention can be applied conventionally employed chemical sensitization methods (e.g., a gold sensitization method as described in U.S. Pat. Nos. 2,399,083; 2,597,856; and 2,597,915; a reduction sensitization method as described in U.S. Pat. Nos. 2,487,850 and 2,521,925, a sulfur sensitization method as described in U.S. Pat. Nos. 1,623,499 and 2,410,689, a sensitization method using metal ions other than silver as described in U.S. Pat. Nos. 2,448,060; 2,566,245 and 2,566,263 or a combination thereof).

In addition, spectrally sensitizing methods conventionally used for color light-sensitive materials can also be used. Suitable examples of spectral sensitizers and methods for their use are disclosed in U.S. Pat. No. 3,397,060 and 3,522,052, British Pat. No. 1,216,203, and German OLS 2,030,326.

Furthermore, there can be incorporated conventionally used stabilizers (e.g., 4-hydroxy-1,3,3a,7-tetrazaindene derivative), an antifogging agent (e.g., a mercapto compound or a benzotriazole derivative), a coating aid, a hardening agent, a wetting agent, a sensitizing agent (e.g., an onium derivative such as the quaternary ammonium salts as described in U.S. Pat. Nos. 2,271,623; 2,288,226 and 2,334,864) and polyalkylene oxide derivatives as described in U.S. Pat. Nos. 2,708,162; 2,531,832; 2,533,990; 3,210,191; and 3,158,484. Also, dyes for anti-irradiation and, as a constituent for the stratum of the color light-sensitive material of the present invention, a filter layer, a mordant-dyeing layer or a hydrophobic dye-containing colored layer can be present.

The light-sensitive emulsion to be used in the present invention is applied to various supports. Suitable supports which can be used are, e.g., a cellulose acetate film, a polyethylene terephthalate film, a polyethylene film, a polypropylene film, a glass plate, a baryta paper, a resin-laminated paper, a synthetic paper and the like. A suitable coating amount of silver ranges from about 0.01 to 50 g/m², of the compound of the formula (I) from about 0.001 to 10 g/m² and of the couplers of the formula (II) to (VI) from about 0.001 to 50 g/m².

The photographic light-sensitive materials of the present invention are development-processed using a color developing solution containing as a color developing agent conventionally employed p-phenylenediamine derivative, p-aminophenol derivative or the like. Preferred p-phenylenediamine derivatives to be used include, e.g., p-amino-N-ethyl-N-$\beta$-(methanesulfoamidoethyl)-m-toluidine sesquisulfate monohydrate, diethylamino-p-phenylenediaminesesquisulfite, p-amino-N,N-diethyl-m-toluidine hydrochloride or p-amino-N-ethyl-N-$\beta$-hydroxyethylaniline sesquisulfate monohydrate. Developers for color negative light-sensitive materials, color negative or positive light-sensitive materials for cinema use, color papers and instant color light-sensitive materials, known in the art, can be used. For example, color development-processing substantially as described in Japanese Patent Publication No. 35749/70; U.S. Pat. No. 3,695,883; Japanese Patent Application Laid Open Nos. 24323/1972 and 37537/1972; German Patent OLS No. 2,238,051; and in H. Gordon, The British Journal of Photography, Nov. 15, 1954, p. 558 set seq; ibid, Sept. 9, 1955, p. 440 et seq; ibid, Jan. 6, 1956, p. 2 et seq; S. Horwitz, ibid, Apr. 22, 1960, p. 212 et seq; E. Gehret, ibid, Mar. 4, 1960, p. 122 et seq; ibid, May 7, 1965, p. 396 et seq; and J. Meech, ibid, Apr. 3, 1959, p. 182 et seq.

When the so-called "DIR couplers or DIR hydroquinone derivatives" are used, it tends to become difficult to bleach the reduced silver with a bleaching solution or to remove the silver halide and reduced silver with a bleach-fixing solution.

The multi-layered color light-sensitive material obtained by the present invention can be silver-bleached using a bleaching solution of a redox potential (Eredox) (defined hereinafter) of −150 mV to 1000 mV containing halide ion and a metal salt or an organic oxidizing agent. Examples of metal salts include the salts of transition metals, particularly the salts or the complex salts of $Ti^{4+}$, $V^{5+}$, $Cr^{6+}$, $Mn^{7+}$, $Mn^{3+}$, $Cu^{2+}$, $Fe^{3+}$, $Co^{3+}$, etc. The organic oxidizing agent includes p-sulfophenylquinone, sulfonaphthoquinone, Bruster-blue radical or Weitz radical. For example, they are described in U.S. Pat. Nos. 2,507,183; 2,529,981; 2,625,477; 2,748,000; 2,810,648; 2,705,201; British Pat. Nos. 1,111,313; 777,635; 1,032,024; 1,014,396; 982,984; Japanese Patent Publication No. 14035/70 and 13944/66.

The Eredox to be used in the present invention is defined as the value measured as follows.

Eredox is measured at 25° C±0.2° C using a composite platinum electrode containing as a reference electrode silver/silver chloride electrode (made by Metrohm Ltd.; model EA-216) and a potentiometer (made by Metrohm Ltd.; model E-436). Examples of the measurement are described below.

| Bleach-Fixing Solution A: | | |
|---|---|---|
| Ferric Salt of Ethylenediaminetetraacetic Acid | 40 | g |
| Ammonium Thiosulfate (70%) | 150 | ml |
| Sodium Sulfite (anhydrous) | 120 | g |
| Water to make | 1000 | ml |
| pH = 6.8, Eredox = −30 mV | | |
| Bleaching Solution B: | | |
| Potassium Bromide | 20 | g |
| Ferric Chloride (6 H₂O) | 41.5 | g |
| Water to make | 1 | l |
| pH = 1.5, Eredox = 720 mV | | |
| Bleaching Solution C: | | |
| Ammonium Bromide | 160 | g |
| Aqueous Ammonia (30%) | 23 | ml |
| Ferric Salt of Ethylenediaminetetraacetic Acid | 130 | g |
| Glacial Acetic Acid | 13.5 | ml |
| Water to make | 1 | l |
| pH = 5.75, Eredox = 170 mV | | |

The multi-layered light-sensitive material obtained by the present invention is preferably processed with a bleaching solution or a bleach-fixing solution having a Eredox of 100 mV to 1000 mV to remove the silver salt.

An experimental example showing this feature of the present invention is given below.

EXPERIMENTAL EXAMPLE

Oxidation potential (Eox) was measured as to the hydroquinone derivatives to be used in the present invention and for comparative compounds. The Eox was measured according to voltammetry, in which Eox means the potential at which an electron is withdrawn from the compound at the anode. The oxidation potential was determined at 25° C in an acetonitrile solution containing as a supporting electrolyte 0.1 N sodium perchlorate using a rotary platinum electrode as the anode and an S.C.E. (Saturated Calomel Electrode) as a reference electrode. The measurement was effected at a concentration of $1 \times 10^{-4}$ to $1 \times 10^{-5}$ mol/l concentration. The measurement was conducted according to the method described in German Patent OLS No. 2,010,762 and 2,219,437.

| Run No. | Compound | Eox (volt) |
|---|---|---|
| (1) | Compound 2 | 0.870 |
| (2) | 2-(1',1',3',3'-Tetramethyl-butyl)hydroquinone | 0.810 |
| (3) | 2,5-Di-(1',1',3',3'-tetramethyl-butyl)hydroquinone | 0.820 |
| (4) | 2-(1',1',3',3'-Tetramethyl-butyl)-5-(1-phenyltetrazol-5-ylthio)hydroquinone | 0.956 |

From the above-described results, it is seen that the reducing property of hydroquinone derivatives is enhanced by replacing the tetramethylbutyl group with an n-octadecylthio group. In this case, the n-octadecylthio group also functions as a ballasting group.

The present invention will now be illustrated by reference to the following non-limiting examples of the present invention, which serve to further clarify the applications and the features of the present invention.

EXAMPLE 1

Four layers were applied to a transparent cellulose triacetate film support as illustrated in FIG. 1 and dried to obtain a sample. The composition and the process for the preparation of each coating solution were as follows.

First Layer: Red-Sensitive Emulsion Layer 1 kg of silver bromoiodide emulsion (silver content: 0.6 mol; iodide content: 6 mol %) was removed and was spectrally sensitized using $4 \times 10^{-5}$ mol/mol silver of Sensitizing Dye I and $1 \times 10^{-5}$ mol/mol silver of Sensitizing Dye II. Separately, 100 g of Coupler A was dissolved in a mixture of 100 cc of tricresyl phosphate and 200 cc of ethyl acetate, and emulsified and dispersed in 1 kg of a 10% gelatin solution using 4 g of sodium nonylbenzenesulfonate. 550 g of the thus obtained Emulsion I was added to the above-described spectrally sensitized emulsion. Further, 2 g of 2,4-dichloro-6-hydroxy-triazine sodium salt was added thereto under stirring as an aqueous solution. The resulting solution was applied in an amount of 1.5 g silver/m².

Second Layer: Interlayer 1 kg of a 10% gelatin aqueous solution was prepared. 50 g of 2,5-di-t-octylhydroquinone was dissolved in 100 cc of tricresyl phosphate and emulsified in 1 kg of a 10% gelatin aqueous solution to disperse as in Emulsion I. 250 g of the resulting emulsion and an aqueous solution containing 2 g of 2,4-dichloro-6-hydroxytriazole sodium salt were added and stirred. The resulting solution was applied in a dry thickness of 1.5 μ.

Third Layer: Blue-Sensitive Emulsion Layer 1 kg of a silver bromoiodide emulsion (silver amount: 0.6 mol; iodide content: 6 mol %) was removed and an emulsion was prepared therefrom in the same manner as described in the first layer. Then, a dispersion of a coupler and a hydroquinone derivative, as shown in Table 1, was added thereto in the amount as shown in Table 1. Thereafter, 2 g of 2,4-di-chloro-6-hydroxytriazine sodium salt was added thereto as an aqueous solution. This emulsion was applied in an amount of 2.0 g silver/m².

Fourth Layer: Protective Layer 0.2 g of sodium nonylbenzenesulfonate was added to 1 kg of a 10% gelatin solution. This solution was then applied in a dry thickness of 1.0 micron.

The sensitizing dyes used for the preparation of the above-described samples were as follows.

Sensitizing Dye I: Anhydro-5,5′-dichloro-3,3′-disulfopropyl-9-ethyl-triacarbocyanine hydroxide pyridinium salt Sensitizing Dye II: Anhydro-9-ethyl-3,3′-di-(3-sulfopropyl)-4,5,4′,5′-dibenzothiacarbocyanine hydroxide triethylamine salt Coupler A: 1-Hydroxy-N-[γ-(2,4-di-tert-amylphenoxy)-propyl]-2-naphthamide Each of the samples was stepwise exposed using a blue light source, followed by uniform exposure using a red light source. Then, they were development-processed at 38° C according to the following processing steps.

| 1. Color Development | 3 min and 30 sec |
|---|---|
| 2. Bleaching | 6 min and 30 sec |
| 3. Washing | 3 min and 15 sec |
| 4. Fixing | 6 min and 30 sec |
| 5. Washing | 3 min and 15 sec |
| 6. Stabilizing | 3 min and 15 sec |

The compositions of the processing solutions used in the respective steps were as follows.

| Color Developer: | | |
|---|---|---|
| Sodium Nitrilotriacetate | 1.0 | g |
| Sodium Sulfite | 4.0 | g |
| Sodium Carbonate | 30.0 | g |
| Potassium Bromide | 1.4 | g |
| Hydroxylamine Sulfate | 2.4 | g |
| 4-(N-Ethyl-N-β-hydroxyethyl-amino)-2-methylaniline Sulfate | 4.5 | g |
| Water to make | 1 | l |
| Bleaching Solution: | | |
| Ammonium Bromide | 160.0 | g |
| Aqueous Ammonia (28%) | 25.0 | ml |
| Iron Salt of Sodium Ethylenediaminetetraacetate | 130 | g |
| Glacial Acetic Acid | 14 | ml |
| Water to make | 1 | l |
| Fixing Solution: | | |
| Sodium Tetrapolyphosphate | 2.0 | g |
| Sodium Sulfite | 4.0 | g |
| Ammonium Thiosulfate (70%) | 175.0 | ml |
| Sodium Bisulfite | 4.6 | g |
| Water to make | 1 | liter |
| Stabilizing Solution: | | |
| Formalin (40%) | 8.0 | ml |
| Water to make | 1 | l |

The results thus obtained are tabulated in Table 1.

TABLE 1

Figure 3:
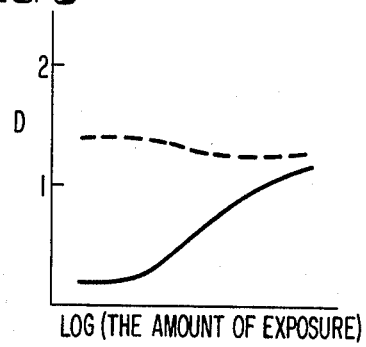
Figure 4:
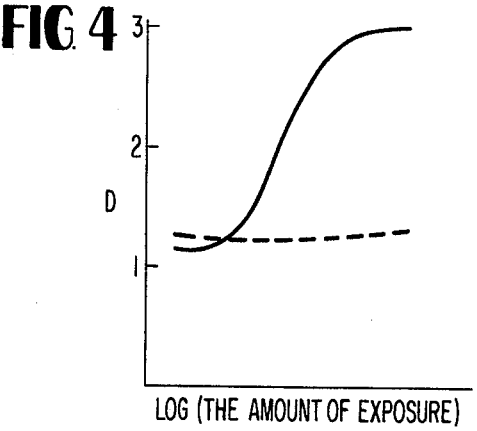
Figure 5:
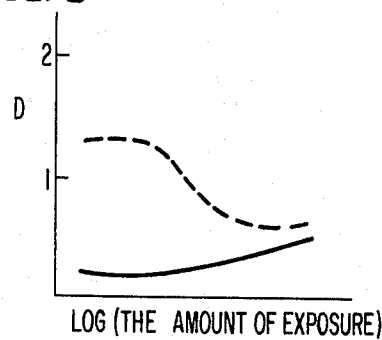

| | Coupler and I.C.C. Hydroquinone Used in the Third Emulsion Layer | | | | |
|---|---|---|---|---|---|
| Sample No. | Coupler | mol/mol silver | I.C.C. Hydroquinone | mol/mol coupler | Result |
| 1 | [Y-7] | 0.10 | Compound 2 | 0.15 | FIG. 2 |
| 2 | Coupler B* | 0.10 | " | " | FIG. 3 |
| 3 | [Y-7] | 0.10 | — | | FIG. 4 |
| 4 | [Y-1] | 0.10 | Compound 2 | 0.15 | FIG. 5 |
| 5 | [Y-1] | 0.10 | — | | FIG. 6 |

*Coupler B: α-(4-Methoxy-benzoyl)-2-chloro-5-[α-(2,4-di-tert-amylphenoxy)-butyramido]acetanilide (4-equivalent coupler)

Figure 2:
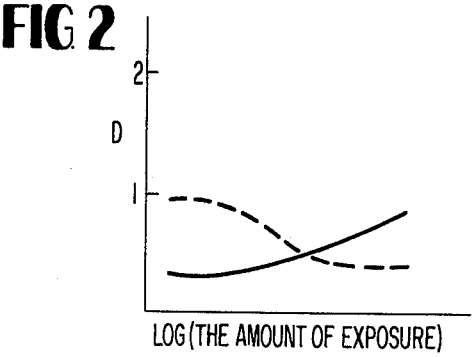
Figure 6:
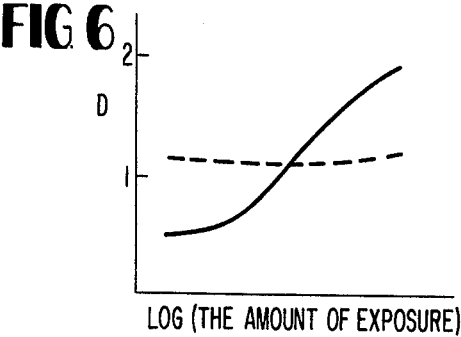

FIGS. 2 and 6 show the characteristic curves obtained, in which the solid line represents the relationship between the blue filter optical density-log (exposure amount) and the dotted line represents the relationship between the red filter optical density-log (exposure), the former corresponding to the characteristic curve of the third layer (containing the yellow coupler) and the latter corresponding to that of the first layer (containing the cyan coupler).

From a comparison of Sample No. 1 with Sample No. 2, it is seen that the use of Coupler [Y-7] provides a markedly strong interlayer interimage effect as compared with the use of Coupler B. From a comparison of Sample No. 4 with Sample No. 5, the strong DIR effect of Compound 2 of the present invention can readily be understood.

EXAMPLE 2

Figure 7:
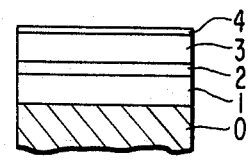

Four layers were applied to a transparent cellulose triacetate film support as shown in FIG. 7, and dried to obtain a sample. The composition and process for the preparation of each coating solution were as follows.

First Layer: Red-Sensitive Emulsion Layer

The same as the first layer in Example 1.

Second Layer: Interlayer

The same as the second layer in Example 1.

Third Layer: Green-Sensitive Emulsion Layer 1 kg of a silver bromoiodide emulsion (the same as in the first layer) was spectrally sensitized using $3 \times 10^{-5}$ mol/mol silver of Sensitizing Dye III and $1 \times 10^{-5}$ mol/mol silver of Sensitizing Dye IV. Separately, 100 g of the coupler shown in Table 2 and a given amount of hydroquinone derivative were used to obtain an emulsion in the same manner as in Emulsion I, to which 2 g of 2,4-dichloro-6-hydroxytriazine sodium salt was added as an aqueous solution under stirring. The resulting solution was applied according to Example 1.

Fourth Layer: Protective Layer

The same as the fourth layer in Example 1.

Sensitizing Dye III: Anhydro-9-ethyl-5,5'-dichloro-3,3'-disulfopropyloxacarbocyanine sodium salt Sensitizing Dye IV: Anhydro-5,6,5,6-tetrachloro-1,1-diethyl-3,3-sulfopropoxyethoxyethylimidazolocarbocyanine hydroxide sodium salt Each of the samples was stepwise exposed using a green light source, followed by uniform exposure using a red light source. The sensitometry according to Example 1 provided the results given in Table 2.

TABLE 2

| | Coupler and I.C.C. Hydroquinone Derivative Used in the Third Emulsion Layer | | | | |
|---|---|---|---|---|---|
| Sample No. | Coupler | mol/mol Ag | I.C.C. Hydroquinone | mol/mol Ag | Results |
| 6 | [M-5] | 0.10 | Compound 10 | 0.015 | FIG. 8 |
| 7 | [M-5] | 0.10 | — | | FIG. 9 |
| 8 | [M-3] | 0.10 | Compound 10 | 0.015 | FIG. 10 |
| 9 | [M-3] | 0.10 | — | | FIG. 11 |
| 10 | Coupler C* | 0.10 | Compound 10 | 0.015 | FIG. 12 |

*Coupler C: 1-(2,4,6-Trichlorophenyl)-3-[3-(2,4-di-tert-amylphenoxyacetamido)-benzamido]-5-pyrazolone (4-equivalent coupler)

Figure 8:
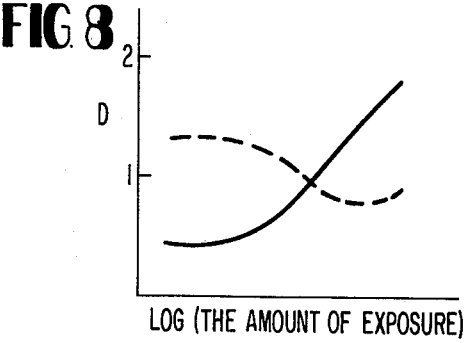

FIGS. 8 to 10 show the characteristic curve obtained, in which the solid line represents the relationship between the green filter optical density-log (exposure amount) and the dotted line represents the relationship between the red filter optical density-log (exposure amount). The features and the effects of the present invention can be seen from a comparison of the results with respect to Sample Nos. 6 and 8 with that obtained with respect to Sample Nos. 7, 9 and, in particular, Sample No. 10.

EXAMPLE 3

A multi-layered color light-sensitive material as illustrated in FIG. 13 comprising a cellulose triacetate support having provided thereon layers having the following compositions was prepared.

First Layer: Antihalation Layer

A gelatin layer containing black, colloidal silver.

Second Layer: Interlayer (ML)

A gelatin layer containing an emulsified dispersion of 2,5-di-t-octylhydroquinone

| Third Layer: First Red-Sensitive Emulsion Layer (RL$_1$) | |
|---|---|
| Silver Bromoiodide Emulsion | (iodide content: 8 mol %) coated in a silver amount of 1.2 g/m$^2$ |
| Sensitizing Dye I (shown in Example 1) | $6 \times 10^{-5}$ mol/mol silver |
| Sensitizing Dye II (shown in Example 1) | $1.5 \times 10^{-5}$ mol silver |
| Coupler A | 0.09 mol/mol silver |
| Coupler [C-5] | 0.02 mol/mol silver |

| Fourth Layer: Second Red-Sensitive Emulsion Layer (RL$_2$) | |
|---|---|
| Silver Bromoiodide Emulsion | (iodide content: 8 mol %) coated in a silver amount of 1.1 g/m$^2$ |
| Sensitizing Dye I | $3 \times 10^{-5}$ mol/mol silver |
| Sensitizing Dye II | $1.2 \times 10^{-5}$ mol/mol silver |
| Compound 14 | 0.02 mol/mol silver |
| Coupler [C-5] | 0.06 mol/mol silver |
| Coupler [A] | 0.08 mol/mol silver |

Fifth Layer: Interlayer (ML)

The same as the second layer.

| Sixth Layer: First Green-Sensitive Emulsion Layer (GL$_1$) | |
|---|---|
| Silver Bromoiodide Emulsion | (iodide content: 8 mol % coated in a silver amount of 1.4 g/m$^2$ |
| Sensitizing Dye III (shown in Example 2) | $3 \times 10^{-5}$ mol/mol silver |
| Sensitizing Dye IV (shown in Example 2) | $1 \times 10^{-5}$ mol/mol silver |
| Coupler [M-8] | 0.05 mol/mol silver |
| Compound 1 | 0.002 mol/mol silver |
| Coupler [M-6] | 0.001 mol/mol silver |

| Seventh Layer: Second Green-Sensitive Emulsion Layer (GL$_2$) | |
|---|---|
| Silver Bromoiodide Emulsion | (iodide content: 6 mol %) coated in a silver amount of 1.5 g/m$^2$ |
| Sensitizing Dye III | $2.5 \times 10^{-5}$ mol/mol silver |
| Sensitizing Dye IV | $0.8 \times 10^{-5}$ mol/mol silver |
| Coupler [M-2] | 0.01 mol/mol silver |
| Coupler [M-8] | 0.02 mol/mol silver |
| Compound 1 | 0.0003 mol/mol silver |

Eighth Layer: Yellow Filter Layer (YFL)

A gelatin layer containing yellow colloidal silver and 2,5-di-t-octylhydroquinone emulsion dispersion.

| Ninth Layer: First Blue-Sensitive Emulsion Layer (BL$_1$) | |
|---|---|
| Silver Bromoiodide Emulsion | (iodide content: 6 mol %) coated in a silver amount of 1 g/m$^2$ |
| Coupler [Y-1] | 0.25 mol/mol silver |

| Tenth Layer: Second Blue-Sensitive Emulsion Layer (BL$_2$) | |
|---|---|
| Silver Bromoiodide Emulsion | (iodide content: 6 mol %) coated in a silver amount of 1.1 g/m$^2$ |
| Coupler [Y-1] | 0.06 mol/mol silver |

| -continued | |
|---|---|
| Compound 1 | 0.002 mol/mol silver |

Eleventh Layer: ADL

A layer provided by coating 1 kg of a super-fine silver bromoiodide emulsion (silver amount: 0.6 mol; iodide content: 1.4 mol %; mean grain size: 0.03 micron) in an amount of 2.3 g silver/m².

Twelfth Layer: Protective Layer (PL)

A gelatin layer containing polymethyl methacrylate particles (diameter: about 1.5 μ).

To each of the above-described layers were added, in addition to the above-described composition, a gelatin-hardening agent, 2,4-dichloro-6-hydroxy-s-triazine sodium salt, a surface active agent (saponin) and a thickening agent (polystyrene sulfonic acid potassium salt) in suitable amounts.

Separately, another sample was prepared in the similar manner except Compound 14 and Compound 1 were not used.

The thus obtained two samples were cut into strips of 35 mm in width and exposed using, in addition to a white light wedge exposure, a blue light source, a green light source and red light source to effect sensitometry according to Example 1. With the sample using Compound 14 and Compound 1, the color stain was less, the graininess was finer and a stronger masking effect, as compared with another sample without these compounds was attained.

The present invention can find application to a color negative light-sensitive material, a color reversal light-sensitive material, a color transparent positive light-sensitive material, a color positive reflection light-sensitive material and a color paper. The present invention can be applied to other recording materials for industrial use which distinctly record color images. In addition, the hydroquinone derivatives of the present invention can be widely applied to black-and-white light-sensitive materials.

While the invention has been described in detail and with reference to specific embodiments thereof, it will be apparent to one skilled in the art that various changes and modifications can be made therein without departing from the spirit and scope thereof.

What is claimed is:

1. A multi-layered color photographic light-sensitive material which provides a negative image upon exposure to an original and subsequent development, said material comprising a support having thereon at least two light-sensitive silver halide emulsion layers which provide images having substantially different hues, wherein at least one of said light-sensitive silver halide emulsion layers or a colloidal layer of said light-sensitive material contains (1) a hydroquinone derivative or a hydroquinone precursor, said derivative and said precursor being substituted with both a heterocyclic monothio group and at least one member selected from the group consisting of an aliphatic monothio group and an aryl monothio group, and said derivative and said precursor having a ballasting group containing 8 or more carbon atoms; and (2) a 2-equivalent coupler and-/or a 4-equivalent anilino-pyrazolone coupler.

2. The multi-layered color photographic light-sensitive material as described in claim 1, wherein said hydroquinone derivative is a compound represented by the following General Formula (Ia);

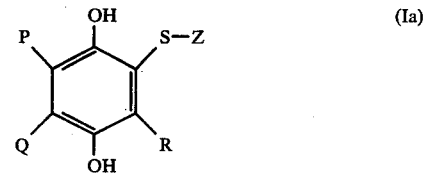

wherein Z represents a tetrazole ring; P, Q, and R each represents a hydrogen atom, an alkyl group, an aryl group, a hydroxy group, a halogen atom, an alkoxy group, or a heterocyclic ring residue, at least one of P, Q and R being a Y—S— residue with Y representing an aliphatic group or an aryl group, and P, Q or R containing a ballasting group having about 8 to 20 carbon atoms.

3. The multi-layered color photographic light-sensitive material as described in claim 1, wherein said color photographic light-sensitive material includes couplers selected from the group consisting of couplers having the General Formula (II);

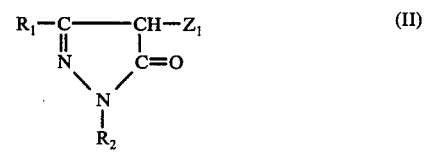

wherein $R_1$ represents an alkyl group, an alkoxy group, an aryloxy group, an aryl group, a heterocyclic ring, an amino group, a carbonamido group, a sulfonamido group, and an ureido group; $R_2$ represents an alkyl group or an aryl group; and $Z_1$ represents a group capable of being eliminated upon color development; couplers having the General Formula (IV);

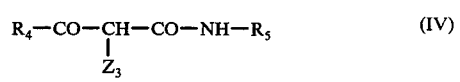

wherein $R_4$ represents an alkyl group or an aryl group; $R_5$ represents an aryl group; and $Z_3$ represents a group capable of being eliminated upon color development; or couplers having the General Formula (V) or (VI);

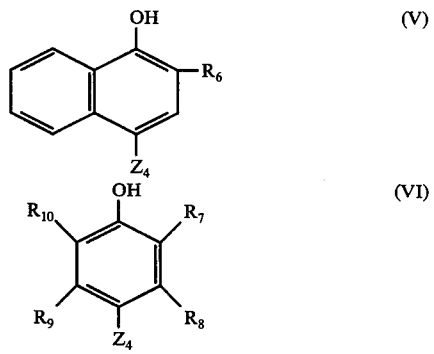

wherein $R_6$ represents a carbamyl group, a sulfamyl group, an alkoxycarbonyl group, or an aryloxycarbonyl group; $R_7$ represents an alkyl group, an aryl group, a heterocyclic group, an amino group, a carbonamido group, a sulfonamido group, a sulfamyl group, or a carbamyl group; $R_8$, $R_9$ and $R_{10}$ each represents a group as defined with respect to $R_7$ and further represents a halogen atom, or an alkoxy group; and $Z_4$ represents a group capable of being eliminated upon color development.

4. The multi-layered color photographic light-sensitive material as claimed in claim 1, wherein said anilinopyrazolone coupler is a coupler having the General Formula (III);

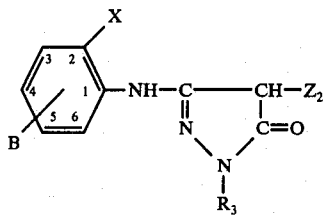

(III)

wherein $R_3$ represents an aryl group or a heterocyclic ring; $Z_2$ represents a hydrogen atom or a group capable of being eliminated upon color development; B represents a ballasting group; and X represents an alkoxy group having from 1 to 18 carbon atoms or a halogen atom.

5. A method for forming color images which comprises developing an exposed multi-layered color photographic light-sensitive material which provides a negative image upon exposure to an original and subsequent development, said material comprising a support having thereon at least two light-sensitive silver halide emulsion layers which provide images having substantially different hues, wherein at least one of said light-sensitive emulsion layers or a colloidal layer of said light-sensitive material contains (1) a hydroquinone derivative or a hydroquinone precursor, said derivative and said precursor being substitued with both a heterocyclic monothio group and at least one member selected from the group consisting of an aliphatic monothio group and an aryl monothio group, and said derivative and said precursor having a ballasting group containing 8 or more carbon atoms; and (2) a 2-equivalent coupler and/or a 4-equivalent anilino-pyrazolone coupler; and bleaching or bleach-fixing the developed multi-layered color photographic light-sensitive material by removing reduced silver or silver salt with a solution having a Eredox of 100 mV to 1000 mV and containing halide ion and $Fe^{3+}$ ion.

* * * * *